United States Patent [19]

Thottathil

[11] Patent Number: 4,594,199

[45] Date of Patent: Jun. 10, 1986

[54] METHOD FOR MAKING PHOSPHINIC ACID INTERMEDIATES

[75] Inventor: John K. Thottathil, Trenton, N.J.

[73] Assignee: E. R. Squibb & Sons, Inc., Princeton, N.J.

[21] Appl. No.: 693,419

[22] Filed: Jan. 22, 1985

Related U.S. Application Data

[63] Continuation-in-part of Ser. No. 533,486, Sep. 19, 1983, abandoned.

[51] Int. Cl.$^4$ .............................. C07F 9/32; C07F 9/65
[52] U.S. Cl. .............................. 260/502.4 R; 558/137; 558/386; 558/167; 546/22; 546/23; 548/112; 548/113
[58] Field of Search ............ 260/970, 502.4 R, 465 R, 260/502.5 D, 502.4 F; 546/22, 23; 548/112, 113

[56] References Cited

U.S. PATENT DOCUMENTS

| | | | |
|---|---|---|---|
| 2,957,931 | 10/1960 | Hamilton et al. | 260/970 |
| 3,914,345 | 10/1975 | Kleiner et al. | 260/970 |
| 4,168,267 | 9/1979 | Petrillo, Jr. | 260/941 |
| 4,316,905 | 2/1982 | Krapcho | 546/256 |
| 4,316,906 | 2/1982 | Ondetti et al. | 424/274 |
| 4,337,201 | 6/1982 | Petrillo | 548/413 |

OTHER PUBLICATIONS

Thottathil et al., "Tetrahydron Letters"; vol. 25, #42, (1984) pp. 4741–4744.

*Primary Examiner*—Anton H. Sutto
*Attorney, Agent, or Firm*—Lawrence S. Levinson; Burton Rodney

[57] ABSTRACT

A method is provided for preparing phosphinic acid prodrug intermediates which are useful in preparing phosphinic acid angiotensin-converting enzyme inhibitors which method includes the step of coupling a phosphonous acid or its ester of the structure

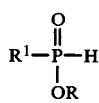

wherein R is H or lower alkyl and $R^1$ is lower alkyl, aryl, arylalkyl, cycloalkyl or cycloalkylalkyl, with a conjugated compound of the structure

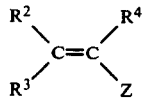

wherein $R^2$, $R^3$ and $R^4$ may be the same or different and each is independently H, lower alkyl or aryl, and Z is $-CO_2R^5$ (wherein $R^5$ is H or lower alkyl),

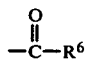

(wherein $R^6$ is H, lower alkyl aryl or arylalkyl),

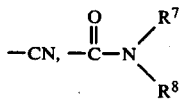

(wherein $R^7$ and $R^8$ are the same or different and are selected from the group consisting of H, lower alkyl, aryl, aryl-lower alkyl, cycloalkyl or cycloalkylalkyl and at least one of $R^7$ and $R^8$ is other than H, or $R^7$ and $R^8$ can be taken together with N to form a 5-, 6- or 7-membered heterocyclic ring

—N , which may or may not include a $COOR^5$ substituent, which 5- or 6-membered N-containing ring may or may not be fused to an aryl ring), in the presence of a silylating agent, to form the phosphonic acid intermediate of the structure

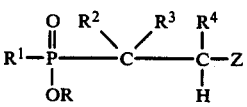

wherein R, $R^1$, $R^2$, $R^3$ and $R^4$ and Z are as defined above.

17 Claims, No Drawings

METHOD FOR MAKING PHOSPHINIC ACID INTERMEDIATES

REFERENCE TO OTHER APPLICATIONS

This application is a continuation-in-part of application Ser. No. 533,486, filed Sept. 19, 1983, now abandoned.

FIELD OF THE INVENTION

The present invention relates to a method for preparing phosphinic acid intermediates having the structure $$R^1-\underset{OR}{\overset{\overset{O}{\|}}{P}}-\underset{|}{\overset{R^2}{C}}-\underset{H}{\overset{R^3\quad R^4}{\underset{|}{C}}}-Z \qquad I$$

wherein
R is H or lower alkyl;
$R^1$ is lower alkyl, aryl, arylalkyl, cycloalkyl, or cycloalkylalkyl;
$R^2$, $R^3$ and $R^4$ may be the same or different and each is independently H, lower alkyl or aryl; and
Z is CN, $-CO_2R^5$ (wherein $R^5$ is H or lower alkyl), $$-\overset{\overset{O}{\|}}{C}-R^6$$

(wherein $R^6$ is H or lower alkyl, aryl or arylalkyl), —CN, or $$-\overset{\overset{O}{\|}}{C}-N\overset{R^7}{\underset{R^8}{\diagdown}}$$

(wherein $R^7$ and $R^8$ are the same or different and can be H, lower alkyl, aryl, aryl-lower alkyl, cycloalkyl or cycloalkylalkyl and at least one of $R^7$ and $R^8$ is other than H, or $R^7$ and $R^8$ can be taken with N to form a 5-, 6- or 7-membered heterocyclic ring

—N⟩ which ring may or may not include a carboxyl substituent $-CO_2R^5$, and which nitrogen containing ring containing 5 or 6 members may or may not include a fused aryl ring, such as a phenyl ring, so that the nitrogen containing ring

—N⟩ together with its fused aryl ring may form indole or tetrahydroisoquinoline systems such as where in the above formulae n' is 0 to 1), which intermediates are useful in the preparation of phosphinic acid angiotensin-converting enzyme inhibitors such as described in U.S. Pat. Nos. 4,168,267 and 4,337,201.

BRIEF DESCRIPTION OF THE INVENTION

The method of the present invention for making phosphinic acid intermediates of formula I includes the step of reacting a phosphonous acid or ester of the structure $$R^1-\underset{OR}{\overset{\overset{O}{\|}}{P}}-H \qquad II$$

wherein R is H or lower alkyl and $R^1$ is lower alkyl, aryl, arylalkyl, cycloalkyl or cycloalkylalkyl, with a conjugated compound of the structure $$\underset{R^3}{\overset{R^2}{\diagdown}}C=C\underset{Z}{\overset{R^4}{\diagup}} \qquad III$$

$R^2$, $R^3$ and $R^4$ may be the same or different and each is H, lower alkyl or aryl, and Z is $CO_2R^5$ (wherein $R^5$ is H or lower alkyl), $$-\overset{\overset{O}{\|}}{C}-R^6$$

(wherein $R^6$ is H, lower alkyl aryl or arylalkyl), CN, or

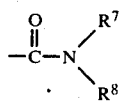

(wherein R⁷ and R⁸ are the same or different and can be H, lower alkyl, aryl, aryl-lower alkyl, cycloalkyl or cycloalkylalkyl and at least one of R⁷ and R⁸ is other than H, or R⁷ and R⁸ can be taken with N to form a 5-, 6- or 7-membered heterocyclic ring

which ring may or may not include a carboxyl substituent —CO₂R⁵, and which 5- or 6- membered N-containing ring may or may not include a fused aryl ring, such as a phenyl ring, which fused systems are exemplified above), in the presence of a silylating agent and an inert organic solvent to form the phosphinic acid intermediate I which may be separated from the reaction mixture and used in the preparation of phosphinic acid angiotensin-converting enzyme inhibitors such as described in U.S. Pat. Nos. 4,168,267 and 4,337,201.

The term "aryl", as used throughout the specification either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl" or "lower alkyl" as used throughout the specification either by itself or as part of a larger group, refers to groups having 1 to 10 carbon atoms. Alkyl groups having 1 to 4 carbon atoms are preferred.

The term "cycloalkyl", as used throughout the specification either by itself or as part of a larger group, refers to groups having 3 to 7 carbon atoms.

The term "alkoxy" or "alkylthio", as used throughout the specification either by itself or as part of a larger group, refers to groups having 1 to 8 carbon atoms. Alkoxy or alkylthio groups having 1 to 3 carbon atoms are preferred.

The term "arylalkyl" or "cycloalkylalkyl", as used throughout the specification either by itself or as part of a larger group, refers to an "alkyl" group as defined above containing an "aryl" or "cycloalkyl" substituent.

The term "alkanoyl" as used throughout the specification either by itself or as part of a larger group, refers to an "alkyl" group as defined above linked to a carbonyl $$(-\overset{O}{\underset{\|}{C}}-)$$

group.

DETAILED DESCRIPTION OF THE INVENTION

In carrying out the method of the invention to prepare compounds of formula I, the phosphonous acid or ester starting material II will be reacted with the conjugated compound in the presence of the silylating agent employing mild conditions, namely, a temperature of within the range of from about 0° C. to about reflux temperature (about 120° C.), and preferably from about 0° C. to about 50° C. The reaction will be carried out for a period ranging from about 2 to about 10 hours and preferably from about 5 to about 8 hours in the presence of an inert organic solvent such as chloroform, acetonitrile, dichloromethane, ethyl ether, tetrahydrofuran or dioxane, and optionally, in the presence of an organic base, such as triethylamine, pyridine or N,N-dimethylamine.

The following reaction sequences illustrate a preferred embodiment of the process of the invention.

A. Where R=H and Z=

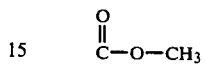

(ester), general case

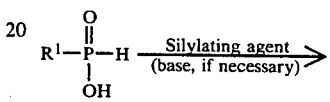

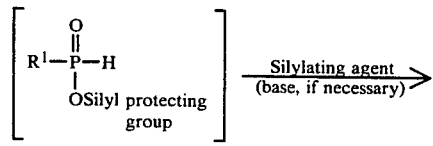

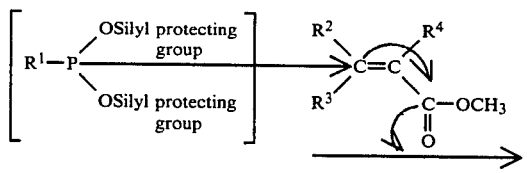

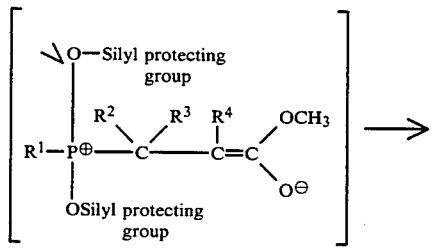

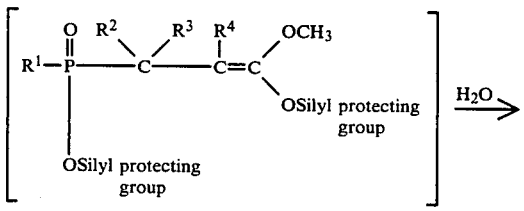

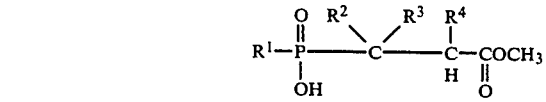

B. Where R=alkyl and Z=

(ester) general case

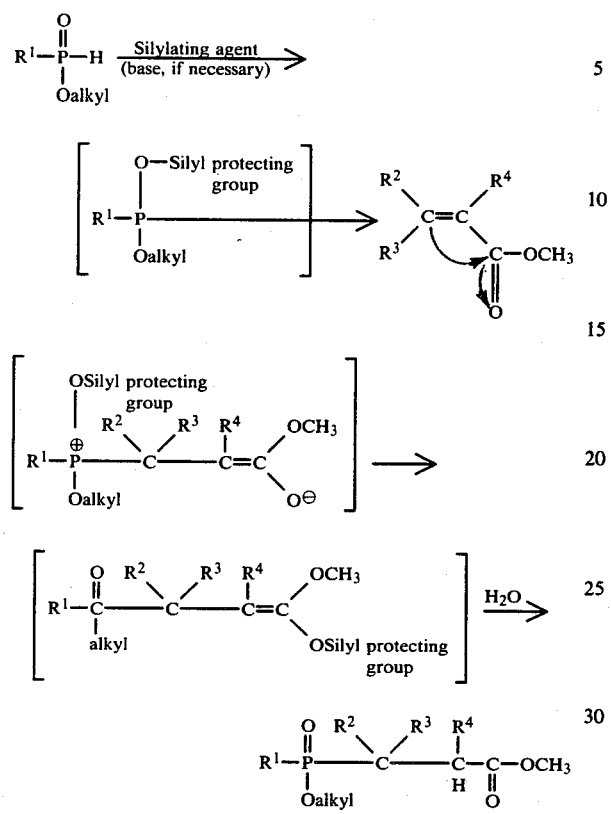

Examples of phosphonous acids or esters II useful as starting materials in carrying out the present invention include, but are not limited to,

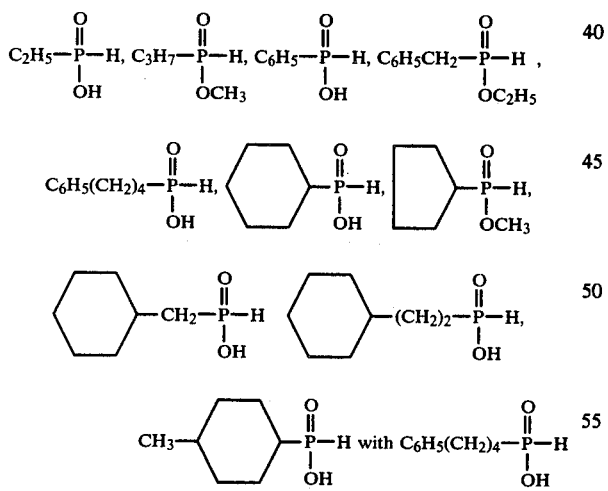

or esters thereof being preferred.

Examples of conjugated compounds II useful in carrying out the present invention include, but are not limited to,

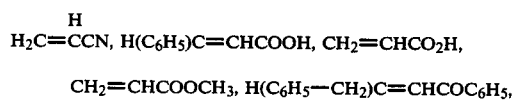

CH₂=CHCOOCH₃, H(C₆H₅—CH₂)C=CHCOC₆H₅,

-continued

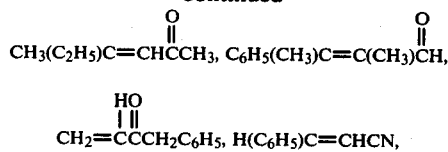

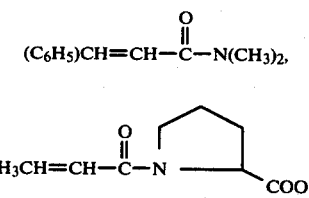

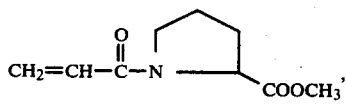

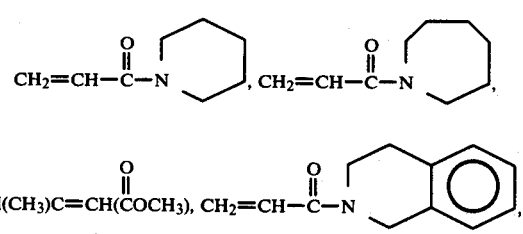

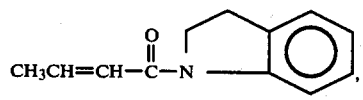

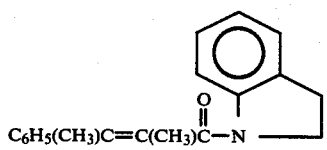

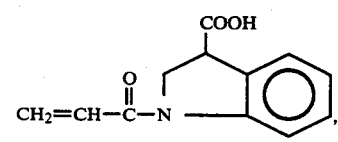

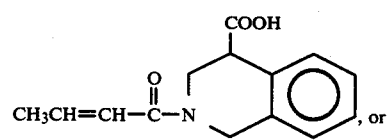

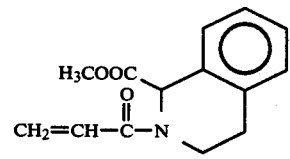

with H₂C=CHCN being preferred.

Examples of silylating agents suitable for use in carrying out the method of the present invention include, but are not limited to, trimethylsilyl chloride and triethylamine, monosilylacetamide, bissilylacetamide, monosilyltrifluoroacetamdie and bissilyltrifluoroacetamide.

Generally, the phosphonous acid or ester II may be employed in a molar ratio to the conjugated compound III of within the range of from about 0.5:1 to about 10:1 and the phosphonous acid or ester III may be employed in a molar ratio to the silylating agent of within the range of from about 0.06:1 to about 2:1. However, usually, in carrying out the method of the invention as described above the amount of phosphonous acid or ester II employed vis-a-vis the conjugated compound III and the silylating agent will depend upon the R substituent in the starting phosphonous acid or ester II and the Z substituent in the conjugated compound III. Thus, where R is lower alkyl and Z is $CO_2$alkyl,

CN or

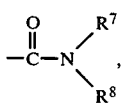

then the phosphonous acid or ester II will be employed in a molar ratio to the conjugated compound III of within the range of from about 0.5:1 to about 10:1, preferably from about 0.75:1 to about 1.25:1, and the phosphonous acid of ester II will be employed in a molar ratio to the silylating agent of within the range of from about 0.1:1 to about 2:1, and preferably from about 0.75:1 to about 1.25:1.

Where in the phosphonous acid or ester II, R is H and in the conjugated compound III, Z is $CO_2R^5$ (wherein $R^5$ is lower alkyl),

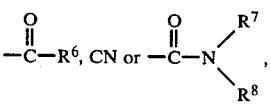

the phosphonous acid or ester II will be employed in a molar ratio to the conjugated compound III of within the range of from about 0.5:1 to about 10:1, preferably from about 0.75:1 to about 1.25:1, and the phosphonous acid or ester II will be employed in a molar ratio to the silylating agent of within the range of from about 0.1:1 to about 1:1, and preferably from about 0.3:1 to about 0.7:1.

Where a phosphonous acid starting material is used, that is in formula II, R is H, and in the conjugated compound III, Z is $CO_2H$, or

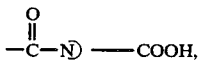

then the phosphonous acid II will be employed in a molar ratio to the conjugated compound III of within the range of from about 0.5:1 to about 10:1, preferably from about 0.75:1 to about 1.25:1, and the phosphonous acid II will be employed in a molar ratio to the silylating agent of within the range of from about 0.06:1 to about 0.5:1, and preferably from about 0.2:1 to about 0.4:1.

Where a phosphonous acid ester of formula II (that is, R is alkyl) is employed and the conjugated compound used is an acid, that is in formula III, Z is $CO_2H$, or

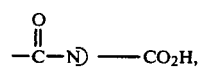

then the phosphonous acid ester II will be employed in a molar ratio to the conjugated compound of within the range of from about 0.5:1 to about 10:1, preferably from about 0.75:1 to about 1.25:1, and the phosphonous acid ester II employed in a molar ratio to the silylating agent of within the range of from about 0.06:1 to about 1:1, and preferably from about 0.3:1 to about 0.7:1.

Where the phosphinic acid intermediate I is obtained in the form of an ester, such ester may be converted to the free acid by conventional means such as by reacting the ester with sodium hydroxide.

The esters of formula I where R is lower alkyl can be obtained from the carboxylic acid compounds, that is wherein R is H, by conventional esterification means, for example, by esterification with diazomethane or by reaction with methyl iodide (or other alkyl halide) and a base such as triethylamine, potassium carbonate and the like.

The following Examples represent preferred embodiments of the present invention. Unless otherwise indicated, all temperatures are expressed in degrees Centigrade.

EXAMPLE 1

3-[Hydroxy-(4-phenylbutyl)phosphinyl]propiononitrile

To a solution of 4-phenylbutyl phosphonous acid (0.44 g, 0.0022 mole) in chloroform (15 ml) was added triethylamine (0.68 ml), trimethyl silylchloride (0.61 ml) and acrylonitrile (0.17 ml) and the reaction mixture was stirred at room temperature for 18 hours; the mixture was poured into crushed ice (15 gm) containing 10 ml 10% HCl acid. It was shaken in a separatory funnel; a chloroform layer was evaporated, and the aqueous layer extracted once with 20 ml chloroform. The combined organic phase was washed with water, dried over anhydrous sodium sulphate and the organic solvent removed on a rotavap to produce the title compound as a highly crystalline solid 0.5 gm (90% yield), m.p. 80°–82° C.

TLC, silica gel, $CH_2Cl_2$:HOAc:MeOH (18:1:1), $R_f = 0.42$.

EXAMPLE 2

3-[Hydroxy-(4-phenylbutyl)phosphinyl]propionic acid

Following the procedure of Example 1, except substituting acrylic acid for acrylonitrile, the title compound is obtained in 61% yield.

TLC, silica gel, $CH_2Cl_2$:HOAc:MeOH (18:1:1), $R_f = 0.19$.

EXAMPLE 3

3-[Hydroxy(phenyl)phosphinyl]-3-phenylpropionic acid, methyl ester

Following the procedure of Example 1, except substituting phenylphosphonous acid for 4-phenylbutyl phosphonous acid and substituting methylcinnamate for acrylonitrile, the title compound is obtained.

EXAMPLE 4

3-(Ethoxyphosphinylpropyl)-3-phenyl-2-methyl-propionic acid

Following the procedure of Example 1, except substituting propylphosphonous acid ethyl ester for 4-phenylbutylphosphonous acid and substituting 2-methyl-3-phenylacrylic acid for acrylonitrile, the title compound is obtained.

EXAMPLE 5

3-[Ethoxy(cyclohexylphosphinyl)]-3-methyl-2-phenyl-propionic acid, methyl ester

Following the procedure as set out in Example 1, except substituting cyclohexylphosphonous acid for 4-phenylbutylphosphonous acid and substituting 2-phenyl-3-methyl-acrylic acid, methyl ester for acrylonitrile, the title compound is obtained.

EXAMPLE 6

3-[Hydroxy(cyclopentylphosphinyl)]-3,3-diethylpropionic acid, methyl ester

Following the procedure as set out in Example 1, except substituting cyclopentylphosphonous acid for 4-phenylbutylphosphonous acid and substituting 3,3-diethyl-acrylic acid methyl ester for acrylonitrile, the title compound is obtained.

EXAMPLE 7

3-[Hydroxy(phenyl phosphinyl)]-3-methyl-propionic acid, methyl ester

Following the procedure as set out in Example 1, except substituting phenylphosphonous acid for 4-phenylbutylphosphonous acid and substituting 3-methyl-acrylic acid, methyl ester for acrylonitrile, the title compound is obtained.

EXAMPLE 8

3-[Hydroxy(benzyl phosphinyl)]-propionic acid, benzyl ester

Following the procedure as set out in Example 1, except substituting benzylphosphonous acid for 4-phenylbutylphosphonous acid and substituting benzyl acrylate for acrylonitrile, the title compound is obtained.

EXAMPLE 9

3-[Hydroxy(propylphosphinyl)]-3,3-dimethylpropiononitrile

Following the procedure as set out in Example 1, except substituting propylphosphonous acid for 4-phenylbutylphosphonous acid and substituting 3,3-dimethyl acrylonitrile for acrylonitrile, the title compound is obtained.

EXAMPLE 10

3-[Methoxy(butylphosphinyl)-3-ethyl-propionic acid, benzyl ester

Following the procedure as set out in Example 1, except substituting butylphosphonous acid methyl ester for 4-phenylbutylphosphonous acid and substituting 3-ethyl-acrylic acid, benzyl ester for acrylonitrile, the title compound is obtained.

EXAMPLE 11

3-[Hydroxy-(4-phenylbutyl)phosphinyl]propionic acid, N,N-dimethylamide

Following the procedure of Example 1 except substituting N,N-dimethylacrylamide for acrylonitrile, the title compound is obtained.

EXAMPLE 12

3-[Hydroxy-(4-phenylbutyl)phosphinyl]propionyl-L-proline, methyl ester

Following the procedure of Example 1 except substituting N-acryloyl-L-proline, methyl ester for acrylonitrile, the title compound is obtained.

EXAMPLE 13

1-[3-Hydroxy-(4-phenylbutyl)phosphinyl]propionyl]indoline-3-carboxylic acid

Following the procedure of Example 1 except substituting 1-acryloyil indoline-3-carboxylic acid for acrylonitrile, the title compound is obtained.

EXAMPLE 14

2-[3-[Hydroxy-(4-phenylbutyl)phosphinyl]propionyl]-1,2,3,4-tetrahydroisoquinoline-1-carboxylic acid Following the procedure of Example 1 except substituting 2-acryloyil-1,2,3,4-tetrahydroisoquinoline-1-carboxylic acid for acrylonitrile, the title compound is obtained.

EXAMPLE 15

2-[3-Hydroxy-(4-phenylbutyl)phosphinyl]propionyl]-1,2,3,4-tetrahydroisoquinoline Following the procedure of Example 1 except substituting 2-acryloyil-1,2,3,4-tetrahydroisoquinoline for acrylonitrile, the title compound is obtained.

EXAMPLE 16

1-[3-[Hydroxy-(4-phenylbutyl)phosphinyl]propionyl]indoline

Following the procedure of Example 1 except substituting 1-acryloyil indoline for acrylonitrile, the title compound is obtained.

EXAMPLE 17

3-[Ethoxy-(4-phenylbutyl)phosphinyl]propionic acid

To a solution of 4-phenylbutyl phosphonous acid, ethyl ester (0.5 g, 0.0022 mole) in chloroform (10 ml) was added triethylamine (0.68 ml, 0.0049 mole), trimethyl silylchloride (0.61 ml, 0.0049 mole) and acrylic acid (0.175 g, 0.0024 mole). The reaction mixture was stirred at room temperature for 18 hours; the mixture was poured into crushed ice (15 gm) containing 10 ml 10% HCl acid. It was shaken in a separatory funnel; a chloroform layer was evaporated, and the aqueous layer extracted once with 20 ml chloroform. The combined organic phase was washed with water and sodium bicarbonate, dried over anhydrous sodium sulfate and the organic solvent removed on a rotavap to produce the title compound as a thick oil (0.4 g, 61% yield).

TLC, silica gel, $CH_2Cl_2$:HOAc:MeOH (20:1:1), $R_f = 0.39$.

EXAMPLE 18

3-[Hydroxy-(4-phenylbutyl)phosphinyl]-2-methyl propiononic acid, methyl ester

To a solution of 4-phenylbutyl phosphonous acid (0.44 g, 0.0022 mole) in chloroform (20 ml) was added triethylamine (0.68 ml, 0.0049 mole), trimethyl silylchloride (0.61 ml, 0.0049 mole) and methyl methacrylate (0.26 ml, 0.0024 mole). The reaction mixture was stirred at reflux temperature for 18 hours; the mixture was poured into crushed ice (15 gm) containing 10 ml 10% HCl acid. It was shaken in a separatory funnel; a chloroform layer was evaporated, and the aqueous layer extracted once with ethyl acetate. The combined organic phase was washed with water and sodium bicarbonate, dried over anhydrous sodium sulphate and the organic solvent removed on a rotavap to produce the title compound as a clear liquid (0.57 g, 88% yield).

TLC, silica gel, $CH_2Cl_2$:HOAc:MeOH (20:1:2), $R_f=0.48$.

EXAMPLE 19

3-[Ethoxy-(4-phenylbutyl)phosphinyl]propiononitrile

To a solution of 4-phenylbutyl phosphonous acid, ethyl ester (0.5 g, 0.0022 mole) in chloroform (10 ml) was added triethylamine (0.341 ml, 0.0024 mole), trimethyl silylchloride (0.303 ml, 0.0024 mole) and acrylonitrile (0.17 ml, 0.0024 mole). The reaction mixture was stirred at reflux temperature for 18 hours; the mixture was poured into crushed ice (15 gm) containing 10 ml 10% HCl acid. It was shaken in a separatory funnel; a chloroform layer was evaporated, and the aqueous layer extracted once with ethyl acetate. The combined organic phase was washed with water, dried over anhydrous sodium sulphate and the organic solvent removed on a rotavap to produce the title compound as a thick oil (0.6 g, 97% yield).

TLC, silica gel, acetone:hexane, $R_f=0.29$.

EXAMPLE 20

3-[Ethoxy-(4-phenylbutyl)phosphinyl]propionic acid, methyl ester

To a solution of 4-phenylbutyl phosphonous acid, ethyl ester (0.5 g, 0.0022 mole) in chloroform (15 ml) was added triethylamine (0.34 ml, 0.0024 mole), trimethyl silylchloride (0.31 ml, 0.0024 mole) and methyl acrylate (0.22 ml, 0.0024 mole). The reaction mixture was stirred at room temperature for 4 hours and then stirred at reflux for 23 hours; the mixture was poured into crushed ice (15 gm) containing 10 ml 5% HCl acid. It was shaken in a separatory funnel; a chloroform layer was evaporated, and the aqueous layer extracted once with 20 ml chloroform. The combined organic phase was washed with water and 5% $NaHCO_3$, dried over anhydrous sodium sulphate and the organic solvent removed on a rotavap to produce the title compound as a clear liquid solid (0.6 g). The crude product was purified through column chromatography (1:1 hexane/acetone eluting solvent system) to yield 0.19 g oil.

EXAMPLE 21

3-[Ethoxy-(4-phenylbutyl)phosphinyl]-3-methylpropionaldehyde

To a solution of 4-phenylbutyl phosphonous acid, ethyl ester (0.5 g, 0.0022 mole) in chloroform (15 ml) was added triethylamine (0.34 ml, 0.0024 mole), trimethyl silylchloride (0.30 ml, 0.0024 mole) and crotonaldehyde (0.20 ml, 0.0024 mole). The reaction mixture was stirred at reflux temperature for 18 hours; the mixture was poured into crushed ice (15 gm) containing 10 ml 5% HCl acid. It was shaken in a separatory funnel; a chloroform layer was evaporated, and the aqueous layer extracted once with 20 ml chloroform. The combined organic phase was washed with water, dried over anhydrous sodium sulphate and the organic solvent removed on a rotavap to produce the title compound as a yellow oil (0.60 g).

EXAMPLE 22

3-[Hydroxy-(4-phenylbutyl)phosphinyl]-3-methylpropionaldehyde

To a solution of 4-phenylbutyl phosphonous acid (0.5 g, 0.0025 mole) in chloroform (15 ml) was added triethylamine (0.77 ml, 0.005 mole), trimethyl silylchloride (0.70 ml, 0.005 mole) and crotonaldehyde (0.23 ml, 0.0025 mole). The reaction mixture was stirred at reflux temperature for 18 hours. The chloroform was removed in vacuo. The residue was diluted with ether and extracted with 5% $NaHCO_3$ solution. The aqueous layer was acidified with concentrated HCl and extracted twice with ether and once with EtOAc. The combined organic phase was washed with water and brine, dried over anhydrous sodium sulphate and the organic solvent removed on a rotavap to produce the title compound as a solid which was dissolved in $CH_3OH$; ether and hexane were added until turbidity. The mixture was kept in a freezer overnight, yield 0.099, m.p. 138° C.

EXAMPLE 23

4-[Hydroxy-(4-phenylbutyl)phosphinyl]-4,4-dimethyl-2-butanone

To a solution of 4-phenylbutyl phosphonous acid (0.5 g, 0.0025 mole) in chloroform (15 ml) was added triethylamine (0.77 ml, 0.005 mole), trimethyl silylchloride (0.70 ml, 0.005 mole) and mesityl oxide (0.32 ml, 0.0025 mole). The reaction mixture was stirred at reflux temperature for 18 hours. $CHCl_3$ was removed in vacuo. The residue was diluted with ether and washed with 5% aqueous $NaHCO_3$ solution. The aqueous layer was acidified with concentrated HCl and extracted twice with ether and once with EtOAc. Organic layers were combined and extracted with brine, dried over $Na_2SO_4$ and solvent was removed to give 0.28 g of the product an an oil.

EXAMPLE 24

4-[Ethoxy-(4-phenylbutyl)phosphinyl]-4,4-dimethyl-2-butanone

To a solution of 4-phenylbutyl phosphonous acid, ethyl ester (1 g, 0.0044 mole) in chloroform (40 ml) was added triethylamine (0.68 ml, 0.0049 mole), trimethyl silylchloride (0.62 ml, 0.0049 mole) and mesityl oxide (0.56 ml, 0.0049 mole). The reaction mixture was stirred at reflux for 18 hours. The solution was washed with $H_2O$, followed by extraction with 5% HCl solution and brine, dried over $Na_2So_4$; solvent was removed in vacuo to give 1.08 g of an oil.

EXAMPLE 25

3-[Hydroxy-(4-phenylbutyl)phosphinyl]propionic acid, methyl ester

To a solution of 4-phenylbutyl phosphonous acid (1 g, 0.005 mole) in chloroform (40 ml) was added triethylamine (1.55 ml, 0.0111 mole), trimethyl silylchloride (1.41 ml, 0.0111 mole) and methyl acrylate (0.50 ml, 0.0055 mole). The reaction mixture was stirred at reflux for 18 hours. CHCl$_3$ was removed in vacuo. The residue was diluted with ether and extracted with 5% aqueous NaHCO$_3$ solution. Aqueous layers were acidified with concentrated HCl and extracted with ether. Organic layers were extracted with brine and dried over Na$_2$SO$_4$. Solvent was removed in vacuo to give 1.26 g of an oil. T-60 $^1$H NMR appeared to characterize product from Michael addition.
$^{13}$C NMR and mass spec. characterization.

EXAMPLE 26

3-[Hydroxy-(4-phenylbutyl)phosphinyl]-3-cyclopentanone

To a solution of 4-phenylbutyl phosphonous acid (1 g, 0.005 mole) in chloroform (40 ml) was added triethylamine (1.55 ml, 0.0111 mole), trimethyl silylchloride (1.41 ml, 0.0111 mol) and 2-cyclopentenone (0.47 ml, 0.0055 mole) and the reaction mixture was stirred at reflux temperature for 18 hours. CHCl$_3$ was removed in vacuo. The residue was diluted with ether and extracted with 5% aqueous NaHCO$_3$. Aqueous layers were acidified with concentrated HCl (a viscous oil and a small amount of solid material came out of solution—low solubility in ether and EtOAc) and extracted with CHCl$_3$. The organic layers were combined and extracted with brine and dried over Na$_2$SO$_4$. The solvents were removed in vacuo to give 1.08 g of product in the form of a yellow viscous oil.

EXAMPLE 27

3-[Ethoxy-(4-phenylbutyl)phosphinyl]-3-cyclopentanone

To a solution of 4-phenylbutyl phosphonous acid (0.5 g, 0.0022 mole) in chloroform (15 ml) was added triethylamine (0.34 ml, 0.0023 mole), trimethyl silylchloride (0.31 ml, 0.0023 mole) and 2-cyclopentenone (0.2 ml, 0.0025 mole) and the reaction mixture was stirred at reflux temperature for 18 hours. The resulting solution was washed with H$_2$O followed by extraction with cold 5% aqueous HCL solution and brine and dried over Na$_2$SO$_4$. Solvent was removed in vacuo to give 0.61 g of a yellow oil.

It will be appreciated that the silylating agent employed in the previous examples, namely, trimethyl silyl chloride employed with triethylamine as a base, may be substituted with any of the silylating agents mentioned hereinbefore, namely, monosilylacetamide, bissilylacetamide, monosilyltrifluoroacetamide, or bissilyltrifluoroacetamide, which silylating agents need not be employed with a separate base.

EXAMPLE 28

2-[3-[Hydroxy-(4-phenylbutyl)phosphinyl]-3-methylpropionyl]-1,2,3,4-tetrahydroisoquinoline-1-carboxylic acid Following the procedure of Example 1 except substituting 2-crotonoyil-1,2,3,4-tetrahydroisoquinoline-1-carboxylic acid for acrylonitrile, the title compound is obtained.

What is claimed is:

1. A method for preparing a phosphinic acid intermediate of the structure $$R^1 - \underset{\underset{OR}{|}}{\overset{\overset{O}{\|}}{P}} - \overset{R^2}{\underset{}{C}} \diagdown \diagup \overset{R^3}{\underset{}{}} \overset{R^4}{\underset{H}{\overset{|}{C}}} - Z$$

wherein R is H or lower alkyl;
R$^1$ is lower alkyl, aryl, arylalkyl, cycloalkyl, or cycloalkylalkyl;
R$^2$, R$^3$ and R$^4$ are the same or different and each is independently H, lower alkyl or aryl;
Z is —CO$_2$R$^5$ (wherein R$^5$ is H or lower alkyl), $$-\underset{}{\overset{\overset{O}{\|}}{C}} - R^6$$

(wherein R$^6$ is H, lower alkyl, aryl or arylalkyl), —CN, or $$-\underset{}{\overset{\overset{O}{\|}}{C}} - N \diagup \overset{R^7}{\diagdown_{R^8}},$$

wherein R$^7$ and R$^8$ are the same or different and are selected from the group consisting of H, lower alkyl, aryl, aryl-lower alkyl, cycloalkyl or cycloalkylalkyl and at least one of R$^7$ and R$^8$ is other than H, or R$^7$ and R$^8$ can be taken together with N to form a 5-, 6- or 7-membered heterocyclic ring $$-N\!\!\!\!\bigcirc$$

which may or may not include a COOR$^5$ substituent, which 5- or 6-membered N-containing ring may or may not be fused to an aryl ring, and
which comprises reacting a phosphonous acid or ester thereof of the structure $$R^1 - \underset{\underset{OR}{|}}{\overset{\overset{O}{\|}}{P}} - H$$

wherein R and R$^1$ are as defined above with a conjugated compound of the structure $$\overset{R^2}{\underset{R^3}{\diagdown}} C = C \overset{R^4}{\underset{Z}{\diagup}}$$

wherein R$^2$, R$^3$, R$^4$ and Z are as defined above, employing a molar ratio of phosphonous acid or ester thereof to the conjugated compound of within the range of from about 0.5:1 to about 10:1, in the presence of a silylating agent employing a molar ratio of phosphonous acid or ester to silylating agent of within the range of from about 0.06:1 to about 2:1 and in the presence of an inert organic solvent to form the phosphinic acid intermediate and separating the phosphinic acid intermediate from the reaction mixture.

2. The method as defined in claim 1 wherein the phosphonous acid is

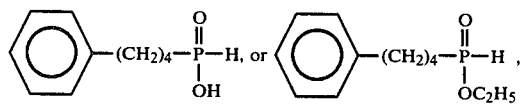

the conjugated compound is $H_2C=CHCN$,

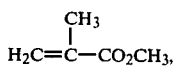

$H_2C=CH-CO_2H$, $H_2C=CH-CO_2CH_3$, $CH_3CH=CHCHO$, $(CH_3)_2C=CHCOCH_3$, and the silylating agent is $(CH_3)_3SiCl$ and $(C_2H_5)_3N$ or bistrimethylsilylacetamide.

3. The method as defined in claim 1 wherein the reaction is carried out in the presence of a base.

4. The method as defined in claim 3 wherein the base is triethylamine, pyridine or N,N-dimethylamine.

5. The method as defined in claim 1 wherein the inert organic solvent is chloroform, acetonitrile, dichloromethane, ethyl ether, tetrahydrofuran or dioxane.

6. The method as defined in claim 1 wherein the silylating agent is trimethyl silylchloride and triethylamine, monosilylacetamide, bissilylacetamide, monosilyltrifluoroacetamide or bissilyltrifluoroacetamide.

7. The method as defined in claim 1 wherein the silylating agent is trimethyl silylchloride and triethylamine.

8. The method as defined in claim 1 wherein in the phosphonous acid or ester, R is lower alkyl, and in the conjugated compound Z is an ester,

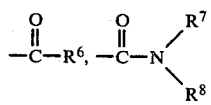

or CN.

9. The method as defined in claim 8 wherein the phosphonous acid ester is employed in a molar ratio to the conjugated compound of within the range of from about 0.5:1 to about 10:1, and the phosphonous acid ester is employed in a molar ratio to the silylating agent of within the range of from about 0.1:1 to about 2:1.

10. The method as defined in claim 1 wherein in the phosphonous acid or ester, R is H and in the conjugated compound Z is an ester,

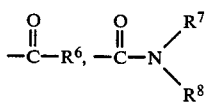

or CN.

11. The method as defined in claim 10 wherein the phosphonous acid is employed in a molar ratio to the conjugated compound of within the range of about 0.5:1 to about 10:1, and the phosphonous acid is employed in a molar ratio to the silylating agent of within the range of from about 0.1:1 to about 1:1.

12. The method as defined in claim 1 wherein in the phosphonous acid or ester, R is lower alkyl, and in the conjugated compound Z is COOH or

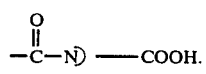

13. The method as defined in claim 12 wherein the phosphonous acid ester is employed in a molar ratio to the conjugated compound of within the range of from about 0.5:1 to about 10:1, and the phosphonous acid ester is employed in a molar ratio to the silylating agent of within the range of from about 0.06:1 to about 1:1.

14. The method as defined in claim 1 wherein in the phosphonous acid or ester, R is H, and in the conjugated compound Z is COOH or

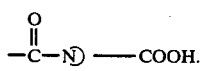

15. The method as defined in claim 14 wherein the phosphonous acid is employed in a molar ratio to the conjugated compound of within the range of from about 0.5:1 to about 10:1, and the phosphonous acid is employed in a molar ratio to the silylating agent of within the range of from about 0.06:1 to about 1:1.

16. The method as defined in claim 1 wherein the reaction between the phosphonous acid or ester and the conjugated compound is carried out at a temperature of within the range of from 0° C. to refluxing temperature.

17. A method for preparing a phosphinic acid intermediate of the structure

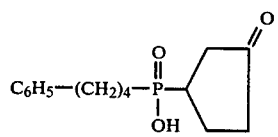

which comprises reading a phosphonous acid or ester thereof of the structure $$C_6H_5-(CH_2)_4-\overset{\overset{O}{\|}}{\underset{OH}{P}}H$$

with a compound of the structure

[cyclopentenone structure]

in the presence of a silylating agent of the structure $(CH_3)_3SiCl$ and an inert organic solvent to form the phosphonic acid intermediate of the structure

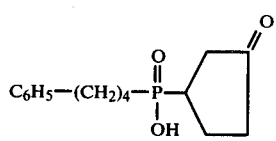
and separating said intermediate from the reaction mixture.
* * * * *

UNITED STATES PATENT AND TRADEMARK OFFICE
CERTIFICATE OF CORRECTION

PATENT NO. : 4,594,199

DATED : June 10, 1986

INVENTOR(S) : John K. Thottathil

It is certified that error appears in the above—identified patent and that said Letters Patent is hereby corrected as shown below:

Column 2 on the title page, fourth structure from the top, "-N" should read --  --.

Column 4, lines 40-49, the structure should read

-- 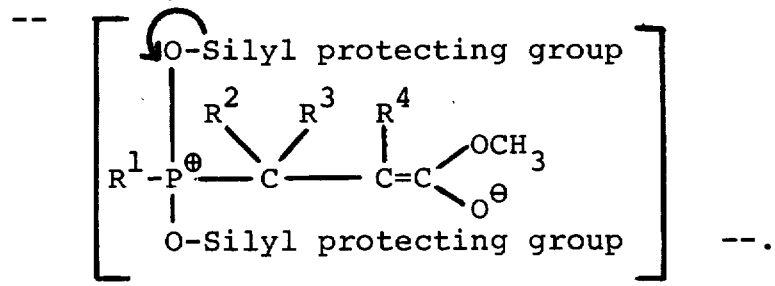 --.

Column 7, line 56, the structure should read

-- 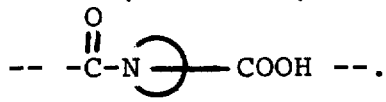 --.

Column 8, line 5, the structure should read

-- 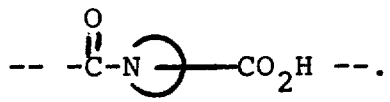 --.

UNITED STATES PATENT AND TRADEMARK OFFICE
CERTIFICATE OF CORRECTION

PATENT NO. : 4,594,199

DATED : June 10, 1986

INVENTOR(S) : John K. Thottathil

It is certified that error appears in the above—identified patent and that said Letters Patent is hereby corrected as shown below:

Column 16, line 24, the structure in Claim 14 should read

Signed and Sealed this

Fourth Day of November, 1986

[SEAL]

Attest:

DONALD J. QUIGG

*Attesting Officer*  *Commissioner of Patents and Trademarks*